United States Patent
Ambati et al.

(10) Patent No.: US 9,506,069 B2
(45) Date of Patent: Nov. 29, 2016

(54) MORPHOLINO-MEDIATED INCREASE IN SOLUBLE FLT-1 EXPRESSION RESULTS IN DECREASED OCULAR AND TUMOR NEOVASCULARIZATION

(71) Applicant: University of Utah Research Foundation, Salt Lake City, UT (US)

(72) Inventors: Balamurali K. Ambati, Sandy, UT (US); Hironori Uehara, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/394,726

(22) PCT Filed: Apr. 19, 2013

(86) PCT No.: PCT/US2013/037465
§ 371 (c)(1),
(2) Date: Oct. 15, 2014

(87) PCT Pub. No.: WO2013/159051
PCT Pub. Date: Oct. 24, 2013

(65) Prior Publication Data
US 2015/0087692 A1    Mar. 26, 2015

Related U.S. Application Data

(60) Provisional application No. 61/635,732, filed on Apr. 19, 2012.

(51) Int. Cl.
*C12N 15/11* (2006.01)
*C12N 15/113* (2010.01)

(52) U.S. Cl.
CPC ....... *C12N 15/1138* (2013.01); *C12N 2310/11* (2013.01); *C12N 2310/3233* (2013.01); *C12N 2320/33* (2013.01)

(58) Field of Classification Search
CPC ................... C12N 2310/3233; C12N 2320/33
See application file for complete search history.

(56) References Cited

U.S. PATENT DOCUMENTS

| | | |
|---|---|---|
| 2003/0032160 A1 | 2/2003 | Kendall et al. |
| 2003/0032609 A1 | 2/2003 | Lee et al. |
| 2003/0229913 A1* | 12/2003 | Habeck ............. A01K 67/0275 800/20 |
| 2005/0287548 A1 | 12/2005 | Bao |
| 2006/0287268 A1 | 12/2006 | Iversen |
| 2008/0269152 A1 | 10/2008 | Verdine et al. |
| 2008/0318857 A1 | 12/2008 | Ambati et al. |
| 2009/0186376 A1 | 7/2009 | Ambati |
| 2010/0136001 A1 | 6/2010 | Sukhatme |
| 2012/0029053 A1 | 2/2012 | Natt |

FOREIGN PATENT DOCUMENTS

WO    WO 2013/074814 A2    5/2013

OTHER PUBLICATIONS

Owen et al. (PLOS-One, published Mar. 15, 2012; vol. 7(3), e33576, 9 pages).*
Abdel-Rahman MH, Yang Y, Salem MM, Meadows S, Massengill JB, et. al. (2010) Investigation of the potential utility of a linomide analogue of treatment of choroidal neovascularization. Exp Eye Res Dec 91(6): 837-843.
Aiello LP, Pierce EA, Foley ED, Takagi H, Chen H, et. al. (1995) Suppression of retinal neovascularization in vivo by inhibition of vascular endothelial growth factor (VEGF) using soluble VEGF-receptor chimeric proteins. Proc Natl Acad Sci U S A 92: 10457-10461.
Albuquerque, R.J., Hayashi, T., Cho, W.G., Kleinman, M.E., Dridi, S., Takeda, A., Baffi, J.Z., Yamada, K., Kaneko, H., Green, M.G., et al. (2009). Alternatively spliced vascular endothelial growth factor receptor-2 is an essential endogenous inhibitor of lymphatic vessel growth. Nat Med 15, 1023-1030.
Alter J, Lou F, Rabinowitz A, Yin H, Rosenfeld J, et.al. (2006) Systemic delivery of morpholino oligonucleotide restores dystrophin expression bodywide and improves dystrophic pathology. Nature Medicine Feb 12(2): 175-7.
Ambati BK, Nozaki M, Singh N, Takeda A, Jani PD, et. al. (2006) Corneal avascularity is due to soluble VEGF receptor-1. Nature Oct. 26; 443: 993-997.
Bertin S, Mohsen-Kanson T, Baqué P, Gavelli A, Momier D, et.al. (2010) Tumor microenvironment modifications induced by soluble VEGF receptor expression in a rat liver metastasis model. Cancer Lett Dec. 8;298(2):264-72.
Bhargava, P., and Robinson, M.O. (2011). Development of second-generation VEGFR tyrosine kinase inhibitors: current status. Curr Oncol Rep 13, 103-111.
Brown DM , Kaiser PK , Michels M, Soubrane G, Heier JS, et.al. (2006) Ranibizumab versus verteporfin for neovascular age-related macular degeneration. N EnglJ Med 355: 1432-1444.
Cao Y, Cao R, Hedlund EM. (2008) R Regulation of tumor angiogenesis and metastasis by FGF and PDGF signaling pathways. J Mol Med Jul.; 86(7): 785-89.
Carmeliet et al, Nature, 2000, 407, pp. 249-257.
Carmeliet et al, Nature, 2011, 473, pp. 298-307.
Ebos, J.M. et al. A naturally occurring soluble form of vascular endothelial growth factor receptor 2 detected in mouse and human plasma. *Mol Cancer Res* 2, 315-326 (2004).
Elkin M, Orgel A, and Kleinman HK (2004) An angiogenic switch in breast cancer involves estrogen and soluble vascular endothelial growth factor receptor 1. J Natl Cancer Inst Jun. 2;96(11):875-8.

(Continued)

*Primary Examiner* — Jon E Angell
(74) *Attorney, Agent, or Firm* — Thorpe North & Western, LLP (57) ABSTRACT

Methods of inhibiting lymphangiogenesis and/or angiogenesis in a subject are provided. In one aspect, for example, a method of inhibiting angiogenesis in a subject can include binding an antisense morpholino to an mRNA splicing site of VEGFR1 selected from exon13_intron13 junction, intron13_exon14 junction, or a combination thereof. In another aspect, the morpholino includes a member selected from VEGFR1_MOe13, VEGFR1_MOi13, or a combination thereof.

16 Claims, 6 Drawing Sheets

(56) References Cited

OTHER PUBLICATIONS

Ellis, L.M., and Hicklin, D.J. (2008). VEGF-targeted therapy: mechanisms of anti-tumour activity. Nat Rev Cancer 8, 579-591.
Fischer, C., Mazzone, M., Jonckx, B., and Carmeliet, P. (2008). FLT1 and its ligands VEGFB and P1GF: drug targets for anti-angiogenic therapy? Nat Rev Cancer 8, 942-956.
Folkman J (1972) Anti-angiogenesis: new concept for therapy of solid tumors. Ann Surg March; 175(3): 409-416.
Gasparini, G (2000) Prognostic Value of Vascular Endothelial Growth Factor in Breast Cancer. Oncologist 5(suppl 1):37-44.
Giovannini M, Aldrighetti D, Zucchinelli P, Belli C, and Villa E (2010) Antiangiogenic strategies in breast cancer management. Crit Rev Oncol Hematol Oct;76(1):13-35.
Goldman, C.K., Kendall, R.L., Cabrera, G., Soroceanu, L., Heike, Y., Gillespie, G.Y., Siegal, G.P., Mao, X., Bett, A.J., Huckle, W.R., et al. (1998). Paracrine expression of a native soluble vascular endothelial growth factor receptor inhibits tumor growth, metastasis, and mortality rate. Proc Natl Acad Sci U S A 95, 8795-8800.
Hasumi Y, Mizukami H, Urabe M, Kohno T, Takeuchi K, et. al. (2002) Soluble FLT-1 expression suppresses carcinomatous ascites in nude mice bearing ovarian cancer. Cancer Res Apr. 1;62(7):2019-23.
Hou X, Kumar A, Lee C, Wang B, Arjunan P, et. al. (2010) PDGF-CC blockade inhibits pathological angiogenesis by acting on multiple cellular and molecular targets. Proc Natl Acad Sci U S A Jul. 6 107(27): 12216-12221.
Kendall, R.L., and Thomas, K.A. (1993) Inhibition of vascular endothelial cell growth factor activity by an endogenously encoded soluble receptor. Proc Natl Acad Sci U S A 90, 10705-10709.
Kinali M, Arechavala-Gomeza V, Feng L, Cirak S, Hunt D et al (2009) Local restoration of dystropin expression with the morpholino oligomer AVI-4658 in Duchenne muscular dystrophy: a single blind, placebo-controlled, dose escalation, proof-of-concept study. Lancet Neurol October; 8(10): 918-928.
Kishuku M, Nishioka Y, Abe S, Kishi J, Ogino H, et.al. (2009) Expression of soluble vascular endothelial growth factor receptor-1 in human monocyte-derived mature dendritic cells contributes to their antiangiogenic property. J Immunol Dec. 15:183(12): 8176-85.
Krzystolik MG, Afshari MA, Adamis AP, Gaudreault J, Gragoudas ES (2002) Prevention of experimental choroidal neovascularization with intravitreal anti-vascular endothelial growth factor antibody fragment. Arch Ophthalmol Mar;120(3):338-46.
Lai CM, Shen WY, Brankov M, Lai YK, Barnett NL, et. al. (2005) Long-Term Evaluation of AAV-Mediated sFlt-1 Gene Therapy for Ocular Neovascularization in Mice and Monkeys. Mol Ther 12(4): 659-668.
Lukason M, DuFresne E, Rubin H, Pechan P, Li Q, et. al. (2011) Inhibition of choroidal neovascularization in a nonhuman primate model by intravitreal administration of an AAV2 vector expression a novel anti-VEGF molecule. Mol Ther Feb; 19(2): 260-5.
Meissner, M., Reichenbach, G., Stein, M., Hrgovic, I., Kaufmann, R., and Gille, J. (2009). Down-regulation of vascular endothelial growth factor receptor 2 is a major molecular determinant of proteasome inhibitor-mediated antiangiogenic action in endothelial cells. Cancer Res 69, 1976-1984.
Miles DW, Chan A, Dirix LY, Cortés J, Pivot X, et. al. (2010) Phase III study of bevacizumab plus docetaxel compared with placebo plus docetaxel for the first-line treatment of human epidermal growth factor receptor 2-negative metastatic breast cancer. J Clin Oncol Jul. 10;28(20):3239-47.

Morcos et al, "Vivo-Morpholinos: A Non-Peptide Transporter Delivers Morpholinos into a Wide Array of Mouse Tissue", BioTechniques, 2008, pp. 613-623, vol. 45, No. 6.
Nieto Y, Woods J, Nawaz F, Baron A, Jones RB, et. al. (2007) Prognostic analysis of tumour angiogenesis, determined by microvessel density and expression of vascular endothelial growth factor, in high-risk primary breast cancer patients treated with highdose chemotherapy. Br J Cancer 97, 391-397.
Nissen LJ, Cao R, Hedlund EM, Wang Z, Zhao X, et.al. (2007) Angiogenic factors FGF2 and PDGFBB synergistically promote murine tumor neovascularization and metastasis. J Clin Invest Oct 117(10): 2766-77.
Ogawa, T., Takayama, K., Takakura, N., Kitano, S., and Ueno, H. (2002). Anti-tumor angiogenesis therapy using soluble receptors: enhanced inhibition of tumor growth when soluble fibroblast growth factor receptor-1 is used with soluble vascular endothelial growth factor receptor. Cancer Gene Ther 9, 633-640.
Ozaki H, Hayashi H, Vinores SA, Moromizato Y, Campochiaro PA and Oshima K (1997) Intraviteral sustained release of VEGF causes retinal neovascularizaiton in rabbits and breakdown of the blood retinal barrier in rabbits and primates. Exp Eye Res 64: 505-517.
Reiter, J.L., and Maihle, N.J. (1996). A 1.8 kb alternative transcript from the human epidermal growth factor receptor gene encodes a truncated form of the receptor. Nucleic Acids Res 24, 4050-4056.
Ruffini F, Failla CM, Orecchia A, Bani MR, Dorio AS, et.al. (2011) Expression of the soluble vascular endothelial growth factor receptor-1 in cutaneous melanoma: role in tumour progression. Br J Dermatol May;164(5):1061-70.
Sela, S., Itin, A., Natanson-Yaron, S., Greenfield, C., Goldman-Wohl, D., Yagel, S., and Keshet, E. (2008). A novel human-specific soluble vascular endothelial growth factor receptor 1: cell-type-specific splicing and implications to vascular endothelial growth factor homeostasis and preeclampsia. Circ Res 102, 1566-1574.
Shibuya, M. (2006). Vascular endothelial growth factor receptor-1 (VEGFR-1/Flt-1): a dual regulator for angiogenesis. Angiogenesis 9, 225-230; discussion 231.
Shibuya, M. Differential roles of vascular endothelial growth factor receptor-1 and receptor-2 in angiogenesis. *J Biochem Mol Biol* 39, 469-478 (2006).
Shibuya, M. Vascular endothelial growth factor-dependent and -independent regulation of angiogenesis. BMB Rep 41, 278-286 (2008).
Summerton, "Morpholino, siRNA, and S-DNA Compared: Impact of Structure and Mechanism of Action on Off-Target Effects and Sequence Specificity", Current Topics in Medicinal Chemistry, 2007, pp. 651-660, vol. 7, Bentham Science Publishers Ltd.
Summerton, J. Morpholino antisense oligomers: the case for an RNase H-independent structural type. Biochim Biophys Acta 1489, 141-158 (1999).
Takahashi, T. & Shibuya, M. The 230 kDa mature form of KDR/Flk-1 (VEGF receptor-2) activates the PLC-gamma pathway and partially induces mitotic signals in NIH3T3 fibroblasts. *Oncogene* 14, 2079-2089 (1997).
Tolentino MJ, McLeod DS, Taomoto M, Otsuji T, Adamis AP and Lutty GA (2002) Pathologic features of vascular endothelial growth factor induced retinopathy in the nonhuman primate. Am J Ophthalmol 133: 373-385.
Vivanco, I., and Mellinghoff, I.K. (2010). Epidermal growth factor receptor inhibitors in oncology. Curr Opin Oncol 22, 573-578.
Wages et al. Biotechniques 1997 23:1116-21.
Wong CG, Rich KA, Liaw LH, Hsu HT, Berns MW. (2001) Intravitreal VEGF and bFGF produce florid retinal neovascularization and hemorrhage in the rabbit. Curr Eye Res Feb 22(2): 140-147.

* cited by examiner

SEQUENCE LISTING

<160> NUMBER OF SEQ ID NOS: 14

<210> SEQ ID NO 1
<211> LENGTH: 25
<212> TYPE: DNA
<213> ORGANISM: Human

<400> SEQUENCE: 1

-continued gttgcagtgc tcacctctga ttgta                                             25

<210> SEQ ID NO 2
<211> LENGTH: 25
<212> TYPE: DNA
<213> ORGANISM: Human

<400> SEQUENCE: 2
gcttcctgat ctagtgaaga aagaa                                             25

<210> SEQ ID NO 3
<211> LENGTH: 25
<212> TYPE: DNA
<213> ORGANISM: Mouse

<400> SEQUENCE: 3 cttttttgccg cagtgctcac ctcta                                            25

<210> SEQ ID NO 4
<211> LENGTH: 25
<212> TYPE: DNA
<213> ORGANISM: Human

<400> SEQUENCE: 4
cctcttacct cagttacaat ttata                                             25

<210> SEQ ID NO 5
<211> LENGTH: 20
<212> TYPE: DNA
<213> ORGANISM: Human

<400> SEQUENCE: 5
ctgcaagatt caggcaccta                                                   20

<210> SEQ ID NO 6
<211> LENGTH: 20
<212> TYPE: DNA
<213> ORGANISM: Human

<400> SEQUENCE: 6 ccttttttgtt gcagtgctca                                                  20

<210> SEQ ID NO 7
<211> LENGTH: 24
<212> TYPE: DNA
<213> ORGANISM: Human

<400> SEQUENCE: 7
aaccagaagg gctctgtgga aagt                                              24

<210> SEQ ID NO 8
<211> LENGTH: 24
<212> TYPE: DNA
<213> ORGANISM: Human

<400> SEQUENCE: 8
caaactccca cttgctggca tcat                                              24

<210> SEQ ID NO 9
<211> LENGTH: 20
<212> TYPE: DNA
<213> ORGANISM: Mouse

```
<400> SEQUENCE: 9
aatggccacc actcaagatt                                               20

<210> SEQ ID NO 10
<211> LENGTH: 21
<212> TYPE: DNA
<213> ORGANISM: Mouse

<400> SEQUENCE: 10
ttggagatcc gagagaaaat g                                             21

<210> SEQ ID NO 11
<211> LENGTH: 20
<212> TYPE: DNA
<213> ORGANISM: Mouse

<400> SEQUENCE: 11
gatcaagttc ccctggatga                                               20

<210> SEQ ID NO 12
<211> LENGTH: 20
<212> TYPE: DNA
<213> ORGANISM: Mouse

<400> SEQUENCE: 12
atgcagaggc ttgaacgact                                               20

<210> SEQ ID NO 13
<211> LENGTH: 24
<212> TYPE: DNA
<213> ORGANISM: Mouse

<400> SEQUENCE: 13
aactttggca ttgtggaagg gctc                                          24

<210> SEQ ID NO 14
<211> LENGTH: 24
<212> TYPE: DNA
<213> ORGANISM: Mouse

<400> SEQUENCE: 14
accagtggat gcagggatga tgtt                                          24
```

MORPHOLINO-MEDIATED INCREASE IN SOLUBLE FLT-1 EXPRESSION RESULTS IN DECREASED OCULAR AND TUMOR NEOVASCULARIZATION

RELATED APPLICATIONS

This application claims the benefit of U.S. Provisional Patent Application Ser. No. 61/635,732, filed on Apr. 19, 2012, which is incorporated herein by reference in its entirety.

GOVERNMENT INTEREST

This invention was made with government support under National Eye Institute Grant No. 5R01EY017950. The United States government has certain rights to this invention.

BACKGROUND OF THE INVENTION

Vascular endothelial growth factor (VEGF) is a signal protein produced by cells that stimulates lymphangiogenesis and angiogenesis. This system is partially responsible for the restoration of the oxygen supply to tissues when blood circulation is inadequate. VEGFs normal function is to create new blood vessels during embryonic development, new blood vessels after injury, in muscle following exercise, and new vessels (collateral circulation) to bypass blocked vessels. VEGF is a sub-family of growth factors, namely the platelet-derived growth factor family of cystine-knot growth factors. They are important signaling proteins involved in both lymphangiogenesis and angiogenesis.

When VEGF is overexpressed, it can contribute to various disease conditions. Solid cancers cannot grow beyond a limited size without an adequate blood supply, and thus cancers that can express VEGF are able to grow and metastasize. Overexpression of VEGF can also cause vascular disease in the retina of the eye and other parts of the body. Drugs such as bevacizumab have been used in an attempt to inhibit VEGF and control or slow those diseases.

Members of the VEGF family stimulate cellular responses by binding to tyrosine kinase receptors (the VEGFRs) on the cell surface, causing them to dimerize and become activated through transphosphorylation, although to different sites, times and extents. The VEGF receptors have an extracellular portion consisting of 7 immunoglobulin-like domains, a single transmembrane spanning region, and an intracellular portion containing a split tyrosine-kinase domain. VEGFR-2 appears to mediate almost all of the known cellular responses to VEGF. The function of VEGFR-1 is less well-defined, although it is thought to modulate VEGFR-2 signaling.

SUMMARY OF THE INVENTION

Various methods and compositions relating to vascular endothelial growth factor receptor 1 (VEGFR1) are provided. In one aspect, for example, a method of inhibiting lymphangiogenesis and/or angiogenesis in a subject can include binding an antisense morpholino to a splicing site of VEGFR1 mRNA such as the exon13_intron13 junction, the intron13_exon14 junction, or a combination thereof, such that the VEGFR1 mRNA is spliced into an sFlt-1 isoform. In another aspect, the morpholino has a sequence similarity to the splicing site of greater than about 75%. In yet another aspect, the morpholino has a sequence similarity to the splicing site of greater than about 95%. Non-limiting examples of appropriate morpholinos can include VEGFR1_MOe13 (SEQ ID 001), VEGFR1_MOi13 (SEQ ID 002), and the like, including a combination thereof. In one specific aspect, the morpholino can have a sequence that has at least about 75% sequence similarity to SEQ ID 001. In yet another aspect, the morpholino can have a sequence that has at least about 95% sequence similarity to SEQ ID 001. In a further aspect, the morpholino can have a sequence of SEQ ID 001. In another aspect, the morpholino can have a sequence that has at least about 75% sequence similarity to SEQ ID 002. In yet another aspect, the morpholino can have a sequence that has at least about 95% sequence similarity to SEQ ID 002. In a further aspect, the morpholino can have a sequence of SEQ ID 002.

In another aspect, a pharmaceutical composition for inhibiting angiogenesis in a subject is provided. Such a composition can include a pharmaceutically effective carrier including a morpholino capable of binding to a splicing site of VEGFR1 mRNA such as the exon13_intron13 junction, the intron13_exon14 junction, or a combination thereof to facilitate increased expression of sFlt-1. Non-limiting examples of appropriate morpholinos can include VEGFR1_MOe13 (SEQ ID 001), VEGFR1_MOi13 (SEQ ID 002), and the like, including a combination thereof. In one aspect, the morpholino can have a sequence similarity to the splicing site of greater than about 75%. In another aspect, the morpholino can have a sequence similarity to the splicing site of greater than about 95%. In another aspect, the morpholino can have a sequence that has at least about 75% sequence similarity to SEQ ID 001. In yet another aspect, the morpholino can have a sequence that has at least about 95% sequence similarity to SEQ ID 001. In a further aspect, the morpholino can have a sequence of SEQ ID 001. In another aspect, the morpholino can have a sequence that has at least about 75% sequence similarity to SEQ ID 002. In yet another aspect, the morpholino can have a sequence that has at least about 95% sequence similarity to SEQ ID 002. In a further aspect, the morpholino can have a sequence of SEQ ID 002.

There has thus been outlined, rather broadly, various features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

DETAILED DESCRIPTION OF THE INVENTION

Definitions

In describing and claiming the present invention, the following terminology will be used in accordance with the definitions set forth below.

The singular forms "a," "an," and, "the" include plural referents unless the context clearly dictates otherwise. Thus, for example, reference to "a morpholino" includes reference to one or more of such morpholinos, and reference to "the oligomer" includes reference to one or more of such oligomers.

As used herein, the term "mRNA" can be used to describe sequences of mRNA and sequences of pre-mRNA, irrespective of the degree of splicing that has occurred in the sequence.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Inhibiting Angiogenesis

Angiogenesis, though a fundamental physiologic process, is a key pathogenetic feature of numerous disease states. At present, therapeutic strategies have limited potential largely due to the fact that the underlying mechanisms of angiogenesis are incompletely understood. Identification of vascular endothelial growth factor receptor (VEGF) as a critical mediator of vessel growth has been an important step to understanding the human condition in terms of the underlying molecular events. For example, VEGF has been shown to be necessary and sufficient for ocular neovascularization. In fact, transgenic mice that over-express human VEGF show widespread ocular neovascularization, and it has also been shown that solid tumor growth requires VEGF expression. However, it is not fully known what specific molecular mediators regulate VEGF expression.

Alternative polyadenylation, considered part of alternative splicing, helps generate diverse mRNA and protein from a limited set of genes. Polyadenylation sites can occur in the 3' untranslated region (3'UTR) of genes and result in different 3'UTRs that can affect mRNA stability and cellular location. Alternate polyadenylation sites can also exist in specific exons or introns of a given gene resulting in functional changes to proteins translated from that gene. Examples of such alternative splicing are seen in VEGFR genes, which can participate in angiogenesis and/or lymphangiogenesis. In one specific example, the VEGFR1 (also referred as Flt-1) gene can produce two functionally distinct protein products, membrane bound VEGFR1 (mbFlt-1) and its isoform soluble VEGFR1 (sFlt-1).

As such, sFlt-1 is an alternatively spliced form of the Flt-1 gene. This alternative splicing event occurs within intron 13 such that sFlt-1 contains the ligand-binding domain, but lacks the membrane-spanning and intracellular kinase domains of the full-length mbFlt-1 protein. As suggested by its structure, sFlt-1 is a potent endogenous inhibitor of VEGF A-induced angiogenesis. While the full complement of sFlt-1 expression and function has not been described, it has been shown to be both necessary and sufficient for maintenance of the avascular cornea. In addition, modulation of sFlt-1 may play a role in the development and treatment of a form of pathologic ocular neovascularization termed choroidal neovasculization (CNV), via modulation of VEGF. Choroidal neovascularization is characterized by choroidal capillary growth through Bruch's membrane beneath the retinal pigmented epithelial (RPE) cell layer. This vascular pathology is most classically seen in exudative or "wet" age-related macular degeneration, the leading cause of vision loss in the western world. Furthermore, sFLT-1 has also been shown to reduce VEGF expression and tumor vascularity in breast adenocarcinoma xenografts. Thus, sFlt-1 represents a potential therapeutic target to reduce aberrant blood vessel growth over a spectrum of diseases.

Current therapies targeting both CNV and tumor vasculature are focused on inhibiting the new vessel growth, and include such modalities as photocoagulation, photodynamic therapy, anti-VEGF intraocular injections, as well as systemic administration of anti-VEGF monoclonal antibody. These approaches have shown some promise; however, they often can induce retinal damage, require repeated intraocular administration, or have recently been contraindicated for use in the case of systemic anti-VEGF therapy for breast adenocarcinoma. Additionally though certainly progress has been made, incomplete efficacy and recurrence is commonly seen with all modalities. Development of novel therapeutic techniques to either augment or circumvent current treatments is necessary to improve both efficacy and the risk profile.

The inventors have discovered that morpholino oligomers directed against splice site targets can modulate splice variant expression. In one aspect, for example, certain morpholino oligomers can alter the splicing of VEGFR1 such that sFlt-1 is favorably expressed. Accordingly, it is possible that morpholino-induced upregulation of sFlt-1 can suppress angiogenesis in clinically relevant models of relevant medical conditions such as, for example, macular degeneration, CNV, breast cancer, and the like. It should be noted that the present scope includes any medical condition that can be treated via such morpholino-induced regulation changes.

In one aspect, for example, a method of inhibiting angiogenesis in a subject is provided. Such a method can include binding an antisense morpholino to a splicing site of VEGFR1 mRNA selected from the group consisting of exon13_intron13 junction, intron13_exon14 junction, or a combination thereof such that the VEGFR1 mRNA is spliced into a sFlt-1 isoform.

Sequence homology between mRNA and a given morpholino can, in some cases, be indicative of the effectiveness of splicing alteration. As such, any degree of homology between a morpholino and a VEGFR1 splice site that affects the expression of sFlt-1 is considered to be within the present scope. In other words, in one aspect a morpholino that increases expression of sFlt-1 in a subject is considered to have a sequence homology to the splice site that is within the present scope. In one specific aspect, however, the morpholino has a sequence similarity to the splicing site of greater than about 75%. In another aspect, the morpholino has a sequence similarity to the splicing site of greater than about 95%. Non-limiting examples of appropriate morpholinos can include VEGFR1_MOe13, VEGFR1_MOi13, as shown below:

```
VEGFR1_MOe13
                                      (SEQ ID 001)
GTTGCAGTGCTCACCTCTGATTGTA

VEGFR1_MOi13
                                      (SEQ ID 002)
GCTTCCTGATCTAGTGAAGAAAGAA
```

Accordingly, in another aspect the morpholino can have a sequence that has at least about 75% sequence similarity to SEQ ID 001. In yet another aspect, the morpholino can have a sequence that has at least about 95% sequence similarity to SEQ ID 001. In a further aspect, the morpholino can have a sequence of SEQ ID 001. Additionally, in one aspect the morpholino can have a sequence that has at least about 75% sequence similarity to SEQ ID 002. In another aspect, the morpholino can have a sequence that has at least about 95% sequence similarity to SEQ ID 002. In yet another aspect, the morpholino can have a sequence of SEQ ID 002.

In other aspects, various pharmaceutical compositions are contemplated. For example, a pharmaceutical composition for increasing expression of sFlt-1 in a subject can include a pharmaceutically effective carrier including a morpholino capable of binding to an a splice site of VEGFR1 mRNA to facilitate increased expression of sFlt-1. Such a composition can be utilized to treat any condition for which an increase in sFlt-1 (or a decrease in mbFlt-1) may be beneficial. It is noted that any morpholino capable of facilitating an increase in sFlt-1 is considered to be within the present scope.

It should be noted that morpholinos and morpholino compositions can be delivered to a genetic target by any known technique, depending in some cases on the nature of the target. For example, for delivery into an RNA-containing solution, morpholinos can be introduced into a buffer solution and added to the solution. For individual cells, cellular tissue, other physiological structures, or other animal or human subjects, morpholinos can be formulated with a carrier that is appropriate for the environment and the mode of delivery. Various modes of delivery are contemplated, which include, without limitation, injection, iontophoresis, passive delivery, or any other effective delivery technique. Any potential transfection technique should thus be considered to be within the present scope. One non-limiting example can include a transfection technique such as nucleofection.

Additional components are also contemplated for inclusion in a morpholino composition, and any component that provides a benefit to the delivery, storage, use, etc. of the composition is considered to be within the present scope. Additionally, such components can vary depending on the intended delivery mode utilized. Concentrations, formulation specifics, ingredient ratios, and the like can be readily determined by those skilled in the art once in possession of the present disclosure.

In one aspect, a pharmaceutical composition for inhibiting angiogenesis in a subject can include a pharmaceutically effective carrier including a morpholino capable of binding to a splicing site of VEGFR1 mRNA such as, for example, exon13_intron13 junction, intron13_exon14 junction, or a combination thereof, to facilitate increased expression of sFlt-1. In one specific aspect, the morpholino can include at least one of SEQ ID 001 or SEQ ID 002. In another aspect, the morpholino can have a sequence similarity to the splicing site of greater than about 75%. In yet another aspect, the morpholino can have a sequence similarity to the splicing site of greater than about 95%. In a further aspect, the morpholino can have a sequence that has at least about 75% or at least about 95% sequence similarity to SEQ ID 001. In one specific aspect, the morpholino can have a sequence of SEQ ID 001. In another aspect, the morpholino can have a sequence that has at least about 75% or at least about 95% sequence similarity to SEQ ID 002. In yet another aspect, the morpholino can have a sequence of SEQ ID 002.

Figure 1A:
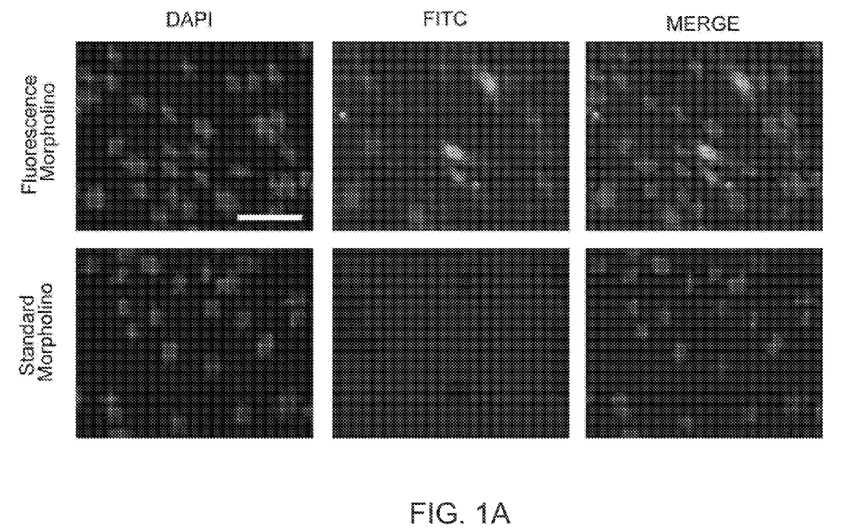
FIG. 1A provides image data showing that VEGFR1_MOe13 localizes to the nucleus and increases sFlt-1 expression in HUVECs in accordance with one embodiment of the present invention.
Figure 1B:
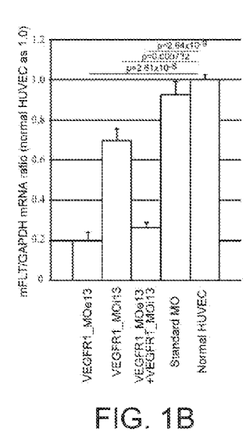
FIG. 1B provides data showing that VEGFR1_MOe13 localizes to the nucleus and increases sFlt-1 expression in HUVECs in accordance with one embodiment of the present invention.
Figure 1C:
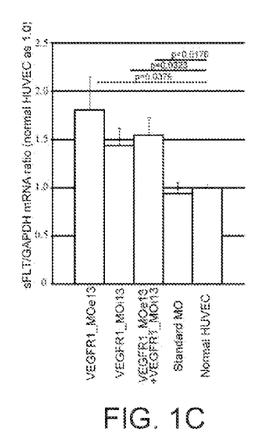
FIG. 1C provides data showing that VEGFR1_MOe13 localizes to the nucleus and increases sFlt-1 expression in HUVECs in accordance with one embodiment of the present invention.
Figure 1D:
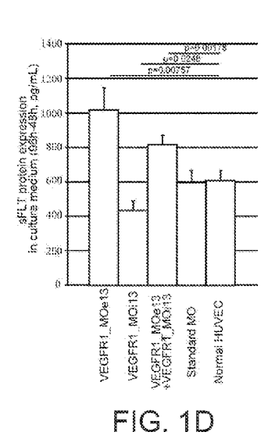
FIG. 1D provides data showing that VEGFR1_MOe13 localizes to the nucleus and increases sFlt-1 expression in HUVECs in accordance with one embodiment of the present invention.
Figure 2A:
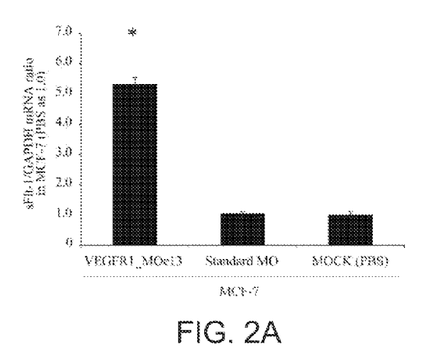
FIG. 2A provides data showing that VEGFR1_MOe13 increases sFlt-1 and decreases mbFlt-1 mRNA in MCF-7 and MBA-MD-231 breast adenocarcinoma cell lines in accordance with another embodiment of the present invention.
Figure 2B:
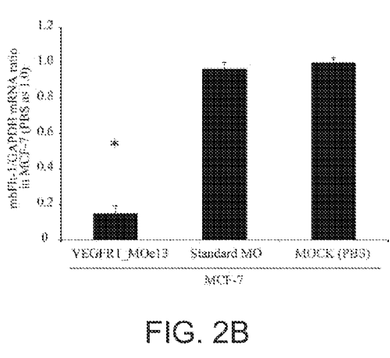
FIG. 2B provides data showing that VEGFR1_MOe13 increases sFlt-1 and decreases mbFlt-1 mRNA in MCF-7 and MBA-MD-231 breast adenocarcinoma cell lines in accordance with another embodiment of the present invention.
Figure 2C:
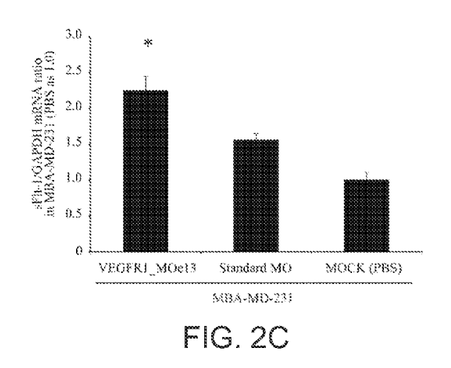
FIG. 2C provided data showing that VEGFR1_MOe13 increases sFlt-1 and decreases mbFlt-1 mRNA in MCF-7 and MBA-MD-231 breast adenocarcinoma cell lines in accordance with another embodiment of the present invention.
Figure 2D:
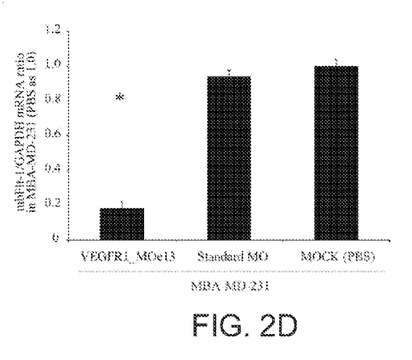
FIG. 2D provides data showing that VEGFR1_MOe13 increases sFlt-1 and decreases mbFlt-1 mRNA in MCF-7 and MBA-MD-231 breast adenocarcinoma cell lines in accordance with another embodiment of the present invention.
Figure 6:
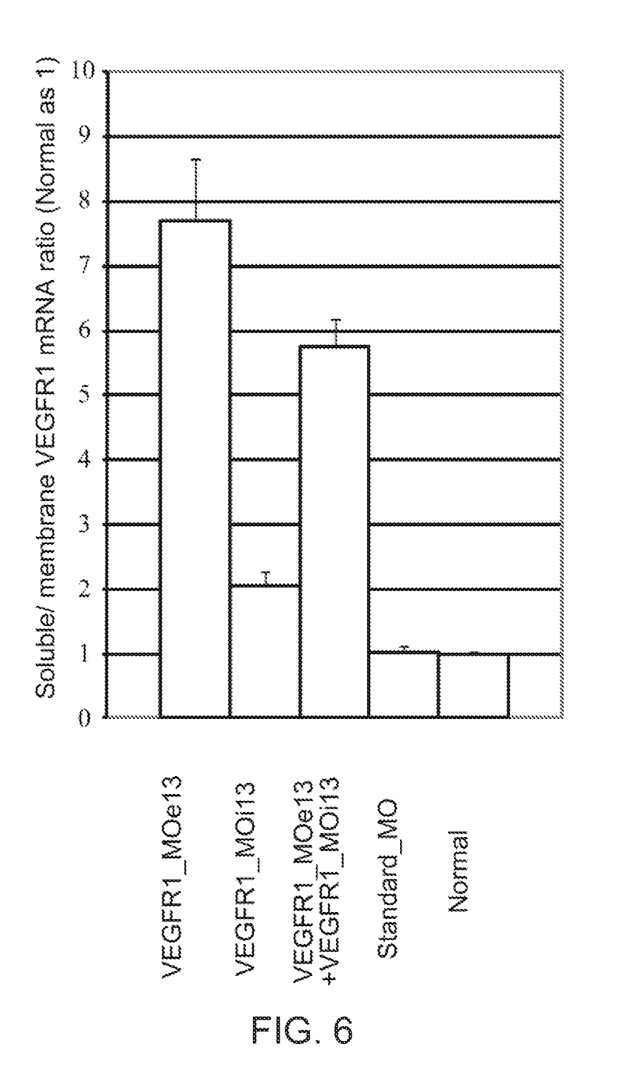
FIG. 6 provides data showing that the sFlt-1/mbFlt-1 ratio increases following electroporation of VEGFR1_MOe13 into HUVECs in accordance with one embodiment of the present invention.

In order to demonstrate the utility of morpholino constructs for modulating sFlt-1 expression, morpholino oligomers were designed targeting the Flt-1 mRNA exon13_intron13 junction (VEGFR1_MOe13 SEQ ID 001) or intron13_exon14 junction (VEGFR1_MOi13 SEQ ID 002). The canonical Flt-1 gene consists of thirty exons in human and mouse. Full-length mRNA from all exons produces the mbFlt-1 protein. By contrast, sFLT-1 utilizes a polyadenylation site within intron13. Therefore, interaction between the morpholino constructs and VEGFR1 pre-mRNA can influence the alternative splicing event such that production of sFlt-1 is favored over mbFlt-1. To directly measure the relationship between the membrane bound and soluble forms of Flt-1 in the presence of VEGFR1_MOe13 and VEGFR1_MOi13, human umbilical vein endothelial cells (HUVEC) were electroporated with targeting or standard morpholino oligomers designed against human VEGFR1. Using this technique MO constructs are found to sufficiently access the nuclear compartment, as is shown in FIG. 1A. Forty-eight hours after electroporation, total RNA is harvested and sFlt-1 and mbFlt-1 mRNA expression is assessed using real-time PCR. It is thus discovered that VEGFR1_MOe13, VEGFR1_MOi13, and a combination of VEGFR1_MOe13 and VEGFR1_MOi13 significantly decrease mbFlt-1 mRNA and increase sFlt-1 mRNA (FIG. 1B-C, and FIG. 6). To determine if the VEGFR1 morpholino constructs also affect sFlt-1 expression at the protein level, sFlt-1 protein in HUVEC culture medium is measured by ELISA in the presence or absence of the VEGFR1 morpholino constructs or control morpholino. VEGFR1_MOe13 increase sFLT-1 protein production as compared with standard morpholino or control PBS conditions (FIG. 1D). In contrast, VEGFR1_MOi13 are less effective, whereas combined delivery of both VEGFR1_MOi13 and VEGFR1_MOe13 show intermediate response, possibly due to competitive interference or reduced efficacy of one morpholino as compared with the other. Thus, morpholino targeting of the Flt-1 mRNA exon13_intron13 junction via VEGFR1_MOe13 expression is efficacious for increasing sFlt-1 and decreasing mbFlt-1 expression in vitro.

FIG. 1 shows that VEGFR1 MOe13 localizes to the nucleus and increases sFlt-1 expression in human endothelial vein cells (HUVEC). FIG. 1A shows fluorescently tagged VEGFR1_MOe13 (F-MO) or standard morpholino (std-MO) electroporated into HUVECs. After 48 hours, fluorescence was assessed using light microscopy. Colocalization with DAPI staining represents nuclear localization of morpholino constructs. HUVECs were electroporated with VEGFR1_MOe13, VEGFR1_MOi13, a combination of VEGFR1_MOe13 and VEGFR1_MOi13, standard_MO. All morpholino sequences were designed to target the human VEGFR1 transcript. FIG. 1B mbFlt-1 mRNA (n=6) or FIG. 1C sFlt-1 mRNA expression (n=6) were assessed using real time PCR. Values were normalized to GAPDH mRNA and normal HUVEC was used as 1.0. In FIG. 1D, sFlt-1 protein expression in culture medium was determined by ELISA (n=3). Data shows sFlt-1 protein at 96 h-48 h. Error bar is S.E.M. Each p-value was calculated by two-tail student's t-test against normal HUVEC. Additionally, FIG. 6 shows the sFlt-1/mbFlt-1 ratio increases following electroporation of VEGFR1_MOe13 into HUVECs. HUVECs were electroporated with VEGFR1_MOe13, VEGFR1_MOi13, a combination of VEGFR1_MOe13 and VEGFR1_MOi13, Standard_MO. All morpholino sequences were designed to target the human VEGFR1 transcript. mbFlt-1 mRNA and sFlt-1 mRNA expression were assessed using real time PCR. Values were normalized to GAPDH mRNA and normal HUVEC was used as 1.0.

To verify that this effect is not cell line specific, the findings were validated in other cellular backgrounds. Although sFlt-1 is predominantly a product of endothelial cells per its role in angiogenesis, it is also expressed by a number of other cell types, including tumor cells. Thus, the inventors sought to determine whether expression of the VEGFR1_MOe13 in MCF7 and MBA-MD-231 breast adenocarcinoma cells would increase sFlt-1 levels. As demonstrated in FIG. 2, electroporation of VEGFR1_MOe13 directed against the human Flt-1 transcript increases sFlt-1 RNA and decreases mbFlt-1 RNA in both adenocarcinoma lines (FIGS. 2A-D).

FIG. 2 shows that VEGFR1 MOe13 increases sFlt-1 and decreases mbFlt-1 mRNA in MCF-7 and MBA-MD-231 breast adenocarcinoma cell lines. MCF7 or MBA-MD-231 human breast adenocarcinoma cells were electroporated with VEGFR1_MOe13, and sFflt-1 mRNA (FIGS. 2A,C) and mbFlt-1 mRNA (FIGS. 2B,D) levels were assessed at 72 hours using real time PCR (n=3). Data were normalized to GAPDH mRNA levels and normal MCF7 or MBA-MD-231 cells were used a 1.0. *p<0.01.

Figure 3A:
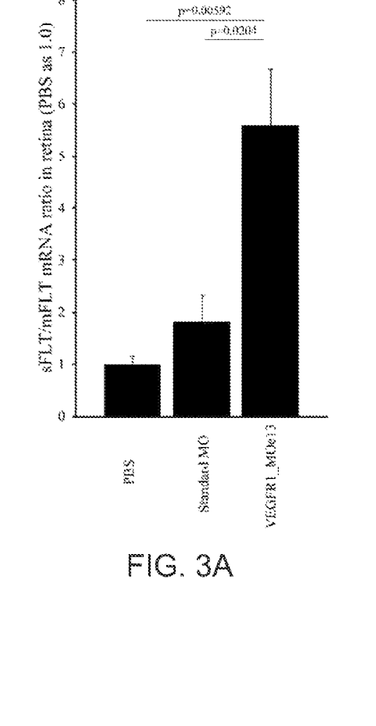
FIG. 3A provides data showing that that VEGFR1_MOe13 inhibits laser-induced CNV in vivo in accordance with yet another embodiment of the present invention.
Figure 3B:
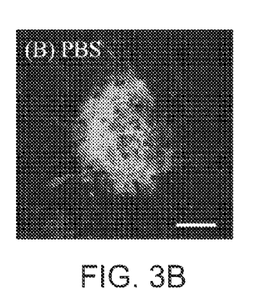
FIG. 3B provides image data showing that that VEGFR1_MOe13 inhibits laser-induced CNV in vivo in accordance with yet another embodiment of the present invention.
Figure 3C:
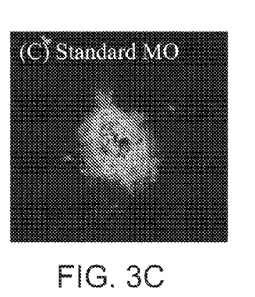
FIG. 3C provides image data showing that that VEGFR1_MOe13 inhibits laser-induced CNV in vivo in accordance with yet another embodiment of the present invention.
Figure 3D:
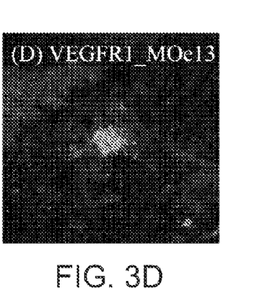
FIG. 3D provides image data showing that that VEGFR1_MOe13 inhibits laser-induced CNV in vivo in accordance with yet another embodiment of the present invention.
Figure 3E:
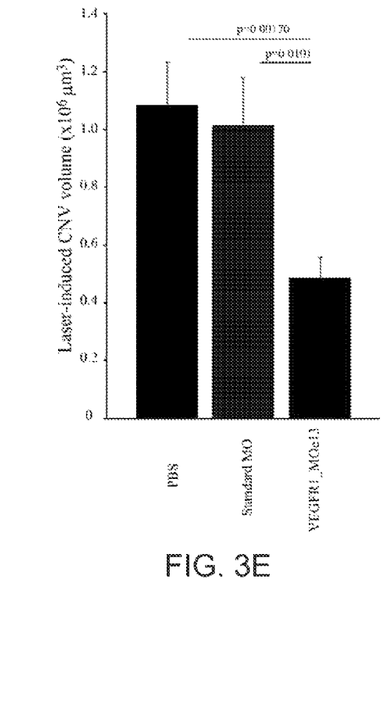
FIG. 3E provides data showing that that VEGFR1_MOe13 inhibits laser-induced CNV in vivo in accordance with yet another embodiment of the present invention.

In order to directly test the efficacy of the VEGFR1_MOe13 for both in vivo activity as well as predicted effects on the process of angiogenesis, a well established murine model of laser-induced choroidal neovascularization that induces significant CNV lesions 1 week after laser injury was utilized. It was hypothesized that expression of VEGFR1_MOe13 in vivo would both increase sFlt-1 levels and lead to suppression of laser-induced CNV. To first evaluate the effectiveness of VEGFR1 MOe13 to modulate sFlt-1 levels in vivo, the sFlt/mbFlt mRNA ratio was examined in the mouse retina 24 hours after injection with PBS, vivo-standard_MO, or vivo-VEGFR1_MOe13 designed to target murine sFlt-1 (the "vivo" denotes modification allowing the MO construct to enter cells in vivo). It was discovered that intravitreal injection of vivo-VEGFR1_MOe13 leads to a significant increase of the sFlt/mbFlt mRNA ratio as compared with PBS or vivo-standard_MO injection (FIG. 3A). Thus, VEGFR1_MOe13 expression is sufficient to increase sFlt-1 expression in vivo. To determine whether VEGFR1_MOe13 expression in vivo could suppress development of CNV in the setting of laser insult, vivo-VEGFR1_MOe13, vivo-standard_MO, or PBS were injected intra-vitreously on day 1 and day 4 after laser photocoagulation. One week after laser photocoagulation, eyes were enucleated and the degree of CNV volume was measured by confocal microscope after isolectin GS-IB4 vasculature staining. CNV volumes were quantified using confocal microscopy. Murine eyes treated with intravitreal vivo-VEGFR1_MOe13 displayed a statistically significant decrease in CNV volume as compared with eyes treated with either vivo-standard morpholino or PBS controls (FIGS. 3B-E). Thus, intra-vitreal injection of vivo-VEGFR1_MOe13 leads to increased levels of sFlt-1 and suppression of laser-induced CNV.

FIG. 3 demonstrates that VEGFR1 MOe13 inhibits laser-induced CNV in vivo. FIG. 3A shows the sFlt/mbFlt mRNA ratio in the retina treated with PBS, Standard_MO, and VEGFR1_MOe13 (n=4). Representative images of laser CNV injected with PBS (FIG. 3B), Standard_MO (FIG. 3C), and VEGFR1_MOe13 (FIG. 3D) designed to target the murine VEGFR1 transcript are shown. FIG. 3E shows the averages of laser CNV volumes (n=11-14). Error bar is S.E.M. p-values were calculated by two-tail student's t test.

In order to demonstrate that the measured effect of reduced CNV following intra-vitreal injection of VEGFR1_MOe13 was specific for an increase in sFlt-1 expression, the inventors knocked-down sFlt-1 expression with AAV2_shsFlt encoding short hairpin RNA (shRNA) targeting sFlt-1 mRNA. Intra-vitreal injections were performed using PBS, AAV2_shNEG (non specific shRNA) or AAV2_shsFlt (shRNA targeting sFlt-1) and laser photocoagulation was performed 2 weeks later. In a consistent fashion with prior studies, on day 1 and 4 following photocoagulation, PBS, vivo-standard_MO, or vivo-VEGFR1_MOe13 constructs were injected into pretreated eyes. It was hypothesized that if increased sFlt-1 was sufficient for suppression of the laser-induced CNV phenotype, co-expression of AAV2_shRNA_sFlt would reverse this effect. In agreement with this hypothesis, it was observed that pre-treatment with AAV2_shsFlt results in reversal of VEGFR1_MOe13-mediated CNV suppression (See FIG. 4). Thus, increased sFlt-1 expression is sufficient to at least partially mediate CNV suppression in the setting of laser-induced injury.

Figure 4:
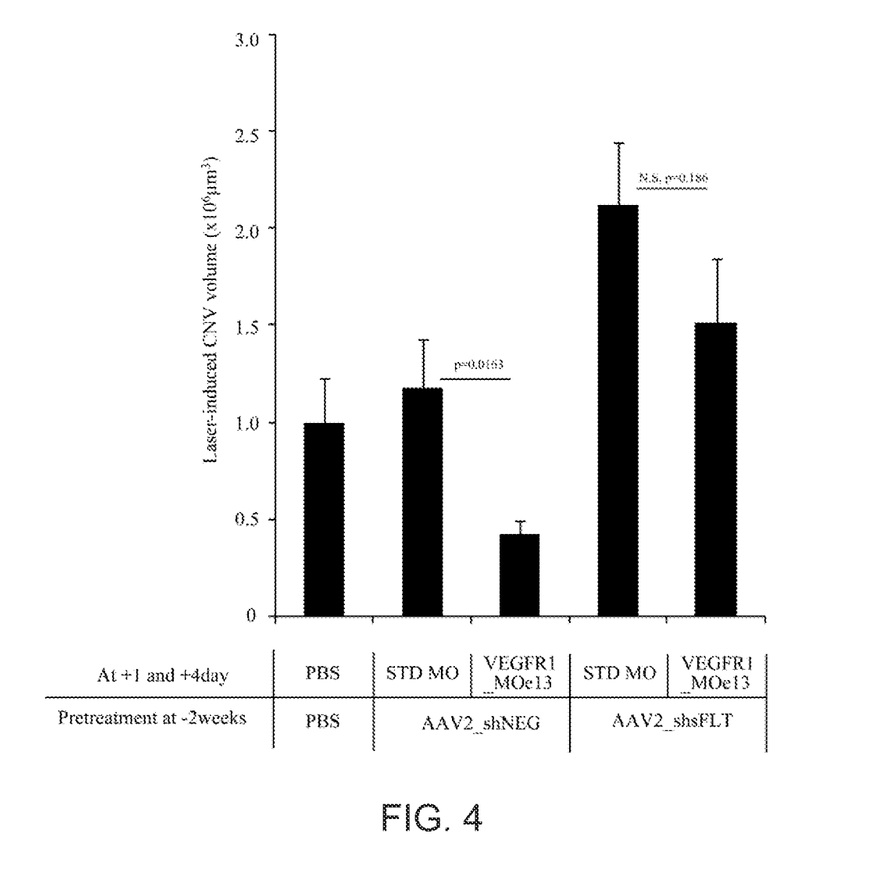
FIG. 4 shows that RNAi targeting sFlt-1 rescues the neovascular phenotype response to laser injury in accordance with another embodiment of the present invention.

FIG. 4 shows that RNAi targeting sFlt-1 rescues the neovascular phenotype response to laser injury. Murine eyes were treated with PBS, AAV2_shNEG or AAV2_shsFLT. After 2 weeks, laser photocoagulation was performed. On 1 day and 4 day after photocoagulation, PBS Standard_MO or VEGFR1_MOe13 were injected. Error bar is S.E.M. N=9-15.

Figure 5A:
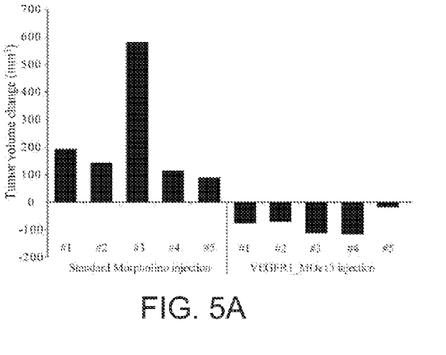
FIG. 5A show tumor regression data in accordance with another embodiment of the present invention.
Figure 5B:
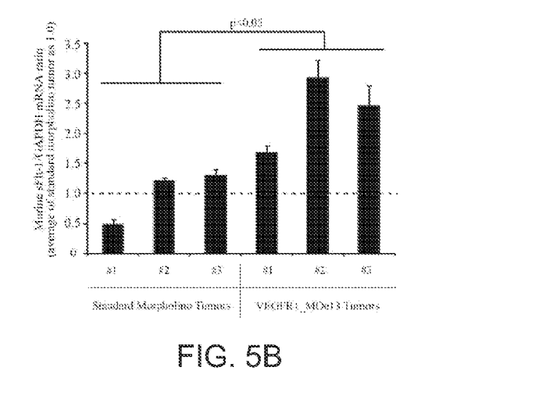
FIG. 5B show tumor regression data in accordance with another embodiment of the present invention.
Figure 5C:
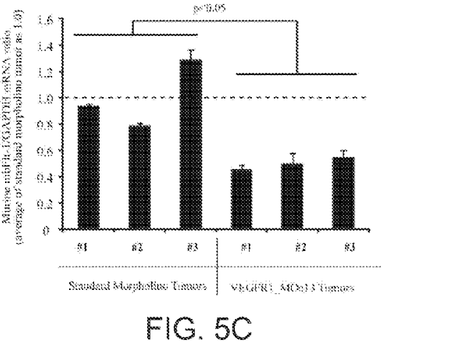
FIG. 5C show tumor regression data in accordance with another embodiment of the present invention.
Figure 5D:
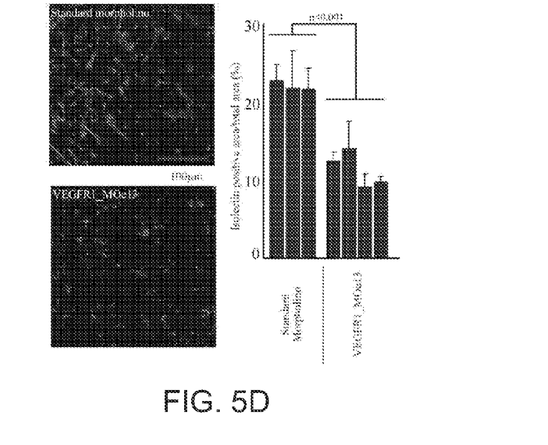
FIG. 5D show tumor regression data in accordance with another embodiment of the present invention.

In order to demonstrate that anti-angiogenic activity of the VEGFR1_MOe13 construct is not limited to the ocular compartment, the inventors then sought to measure its efficacy in the setting of malignancy-associated neovascularization. Tumor vasculature is a rapidly emerging therapeutic target. As such, this model represents an attractive context in which to apply technologies designed to inhibit neovascularization. Within the context of malignancy, breast adenocarcinoma is known to demonstrate marked dependence on VEGF signaling for sustained neovascularization and growth. In fact, VEGF inhibition has been shown to reduce tumor growth in both the experimental as well as the clinical setting. The inventors hypothesized that treatment of MBA-MD-231 human breast adenocarcinoma xenograft tumors with vivo-VEGFR1_MOe13 would result in increased levels of soluble Flt-1 and a subsequent decrease in neovascularization and tumor regression. To directly test this hypothesis, female nude mice were inoculated as described. Xenografts were permitted to grow for 14 days. Tumors were then directly injected with either murine vivo-VEGFR1_MOe13 or vivo-standard morpholino. Injections and tumor volume assessments were performed bi-weekly for a duration of 4 weeks. It was found that treatment of xenograft tumors with vivo-VEGFR1_MOe13 led to tumor regression when compared with standard morpholino treatment (p=0.04) (FIG. 5A). Furthermore, murine sFlt-1 mRNA transcript levels were increased and mbFlt-1 mRNA levels decreased in treatment tumors at the conclusion of the 4 week treatment period as compared with control tumors when assessed using real-time PCR (FIGS. 5B-C). Additionally, to determine whether vascular density was decreased in tumors treated with vivo-VEGFR1_MOe13 injection, tumor vasculature was stained with GS-IB4 and vessel density quantified using fluorescence microscopy following the 4 week treatment period. Tumors treated with the vivo-VEGFR1_MOe13 construct demonstrated a statistically significant decrease in vascular density (FIG. 5D).

As has been described, neovascularization is a common pathological process underpinning numerous disease states. Elucidation of key molecular mediators has allowed for the development of therapeutic strategies targeting the underlying molecular processes. The morpholino oligomer VEGFR1_MOe13 is designed to target the Flt-1 mRNA exon13_intron13; therefore, interaction between VEGFR1_MOe13 and VEGFR1 pre-mRNA influences the alternative splicing event such that production of sFlt-1 is promoted.

The previous has demonstrated that expression of VEGFR1_MOe13 both in vitro and in vivo results in elevated levels of sFlt-1 and decreased mbFlt-1. Furthermore, these data show that VEGFR1_MOe13-mediated increase in sFlt-1 within the retina can prevent choroidal neovascularization following laser photocoagulation. Finally, the data indicate that this phenotype is attributable to increased sFlt-1 expression, as co-treatment with sFlt-1-RNAi negates this effect. Thus, sFlt-1 expression is both necessary and sufficient for suppression of laser-induced CNV. Taken together these data indicate that modulation of sFlt-1 expression in the clinical setting has potential therapeutic value. This represents great promise when considering the over 7 million patients in the US alone with non-exudative age related macular degeneration (ARMD) currently "at risk" for development of CNV.

Angiogenesis in the form of aberrant neovascularization can be fundamental to the pathophysiology of other disease states as well. Notably, new blood vessel formation is required for sustained solid tumor growth. As noted, breast adenocarcinoma is dependent on sustained neovascularization both in animal and human studies. As a "proof of principle" for broad applicability of morpholino-mediated Flt-1 modulation in the treatment of neovascular disease, it was demonstrate that intra-tumoral injection of VEGFR1_MOe13 leads to increased intra-tumoral levels of sFlt-1 and decreased mbFlt-1. Furthermore, breast adenocarcinoma xenografts expressing elevated levels of sFlt-1 demonstrate a blunted neovascular response and regress once established as compared with control tumors. Thus, modulation of sFlt-1 expression using morpholino technology represents a therapeutic tool with broad applicability across a spectrum of neovascular disease.

Taken together, these data indicate that morpholino expression is a viable tool for modulating the expression of Flt-1, i.e., the balance between membrane and soluble forms of this transcript. In this system, these data indicate that morpholino interference at the Flt-1 mRNA exon13_intron13 junction leads to a high amount of sFlt1 production. Expression of the VEGFR1_MOe13 construct is effective in at least two independent disease models, choroidal neovascularization and breast adenocarcinoma. In both, aberrant vasculature and disease burden are reduced. Given the highly divergent roles of Flt1 isoforms, morpholino oligos show promise in a variety of physiologic settings and disease states to act as an "exogenous switch" to modulate angiogenesis.

It should be noted that morpholinos and morpholino compositions can be delivered into a cell, cells, or subject by any known technique, including, without limitation, injection, iontophoresis, passive delivery, electroporation, and the like. Any transfection technique should thus be considered to be within the present scope. One non-limiting example can include a transfection technique such as nucleofection.

Numerous methods of use for the latent polyadenylation system are contemplated, and any such use is considered to be within the present scope. Non-limiting examples of such uses can include various cancer conditions, ocular conditions, rheumatoid arthritis, and any other conditions whereby a morpholino is capable of affecting latent polyadenylation to produce a beneficial effect. Numerous physiological effects can thus be generated depending on the target site of such a procedure. Non-limiting examples of cancer conditions can include breast cancer, colon cancer, lymphoma, prostate cancer, leukemia, and the like. Non-limiting examples of ocular conditions include diabetic retinopathy, macular degeneration, and the like. For example, the anti-sense morpholino oligomer directed against the exon13-intron13 junction that increases sFlt-1 and decreases mbFlt-1 from the VEGFR1 gene can be used to treat various ocular conditions. In one aspect relating to ocular delivery, morpholino injection into the intravitreous cavity can suppress laser choroidal neovascularization (CNV) while increasing sFlt-1 in the intravitreous cavity.

It should be noted that a morpholino composition can be administered to a subject by any known technique, and any such delivery pathway is considered to be within the present scope. Non-limiting examples can include oral compositions, injectable compositions, topical compositions, iontophoretic compositions, and the like, including combinations thereof.

Methods Summary:
Constructs and Reagents:

In vivo morpholino constructs are designed to target murine intron/exon 13 junction of the FLT-1 transcript denoted VEGFR1_MOe13 and VEGFR1_MOi13. Constructs are chemically modified such that they can easily diffuse to access the intracellular compartment. For use in xenograft assays, VEGFR1_MOe13 morpholino constructs are suspended in sterile PBS and used at a concentration of 400 ng/dose. Each dose is equal to about 50 μl total volume.

A standard morpholino targeting the murine beta-globin subunit2 is used as a control and prepared at the same concentration. Morpholino sequences are as follows:

```
Human VEGFR1_MOe13
                                        (SEQ ID 001)
GTTGCAGTGCTCACCTCTGATTGTA Human VEGFR1_MOi13
                                        (SEQ ID 002)
GCTTCCTGATCTAGTGAAGAAAGAA Mouse VEGFR1_MOe13
                                        (SEQ ID 003)
CTTTTTGCCGCAGTGCTCACCTCTA STD MO
                                        (SEQ ID 004)
CCTCTTACCTCAGTTACAATTTATA
```

$2.5 \times 10^9$ GC of AAV.shRNA.sFlt-1 are injected per experimental condition.

Cell Culture:

Primary human umbilical vein endothelial cells (Lonza, Walkersville, Md., USA) are cultured in EBM with EGM SingleQuot Kit supplements and growth factors according to the manufacturer's instructions (Lonza, Walkersville, Md., USA). To prevent loss of endothelial cell properties, cell cultures are limited to passage number 4 to 7. MBAMD-231 human breast adenocarcinoma cells were obtained from the laboratory of Dr. Bryan Welm MD at the Huntsman Cancer Institute, SLC, Utah and maintained in RPMI culture medium containing 10% FBS. MCF7 human breast adenocarcinoma cells were obtained for the laboratory of Dr. Alana Welm PhD at the Huntsman Cancer Institute, SLC, Utah and maintained per ATCC medium recommendations.

Morpholino Delivery to Cultured Cells and Total RNA Extraction 10 ng of morpholinos are delivered to the nucleus by nucleofection using a Basic Nucleofector Kit for Primary Mammalian Endothelial Cells (Amaxa, Gaithersburg, Md., USA), program A-034 for HUVEC. For one nucleofection, $1 \times 10^6$ cells are used and plated on a 6-well plate. After 2 days of culture, cells are trypsinized and total RNA is extracted using a RNeasy mini kit (Qiagen, Valencia, Calif., USA)]. RNA concentrations are determined by 260 nm absorption measured with a spectrophotometer.

Complementary DNA Synthesis and Quantification with Real-Time PCR

Complementary DNA (cDNA) are synthesized from approximately 400 ng total RNA using an Omniscript RT kit (Qiagen, Valencia, Calif., USA) and Oligo-dT primer (dT2) according to the manufacturer's instructions. Real-time PCR is performed using a QuantiTect SYBR Green PCR Kit (Qiagen, Valencia, Calif., USA) and an aliquot 1:1 of cDNA solution. The primer sequences used for human sequence real-time PCR are as follows:

```
VEGFR1_F1:
                                        (SEQ ID 005)
5'-CTGCAAGATTCAGGCACCTA-3'

VEGFR1_R1:
                                        (SEQ ID 006)
5'-CCTTTTTGTTGCAGTGCTCA-3'
```

-continued

VEGFR1_F2:
(SEQ ID 007)
5'-AACCAGAAGGGCTCTGTGGAAAGT-3'

VEGFR1_R2:
(SEQ ID 008)
5'-CAAACTCCCACTTGCTGGCATCAT-3'

The combination of VEGFR1_F and R1 is designed to detect the soluble form of human VEGFR1. The combination of VEGFR1_F2 and R2 is designed to detect the membrane form of human VEGFR1.

The primer sequences used for murine sequence real-time PCR are:

VEGFR1_F1:
(SEQ ID 009)
5'-AATGGCCACCACTCAAGATT

VEGFR1_R1:
(SEQ ID 010)
5'-TTGGAGATCCGAGAGAAAATG

VEGFR1 F2:
(SEQ ID 011)
5'-GATCAAGTTCCCCTGGATGA

VEGFR1_R2:
(SEQ ID 012)
5'-ATGCAGAGGCTTGAACGACT

Gapdh_F:
(SEQ ID 013)
5'-AACTTTGGCATTGTGGAAGGGCTC

Gapdh_R:
(SEQ ID 014)
5'-ACCAGTGGATGCAGGGATGATGTT

The combination of VEGFR1_F1 and R1 is designed to detect the soluble form of murine VEGFR1. The combination of VEGFR1_F2 and R2 is designed to detect the membrane form of murine VEGFR1. Real-time PCR conditions: 50° C. for 2 minutes, 95° C. for 10 minutes, followed by 40 cycles of 94° C. for 15 seconds, 55° C. for 30 seconds, and 72° C. for 30 seconds.

Laser Induced Choroidal Neovascularization

Laser photocoagulation (532 nm, 150 mV, 100 ms, 100 μm; NIDEK MC-4000) is performed on both eyes (2 to 5 spots per eye). After enucleating the eyes, sclera/choroid/RPE complex are fixed in 4% paraformaldehyde for 2 hours at 4 OC. After blocking in 5% FBS/PBS with 0.02% tritonX-100 and 2 mM MgCl2, samples are stained with 5 μg/ml Alexa488 and Alexa546 conjugated isolectin GS-IB4 (Invitrogen Corporation, Carlsbad, USA) overnight. After washing the samples are flat mounted on glass slides. CNV volume is measured by scanning laser confocal microscopy (Olympus America Inc., Center Valley, USA). These animal studies are performed under IACUC protocol approval number 09-03005 approved by the Committee on the Ethics of Animal Experiments at the University of Utah. All interventions are performed either under sodium pentobarbital anesthesia or after animals were humanely euthanized.

Xenograft Analysis:

$3 \times 10^6$ MBA-MD-231 human breast adenocarcinoma cells are injected subcutaneously into the flanks of female nude mice. Following a standardized 2 week inoculation period, xenograft tumors are injected biweekly for a total duration of 4 weeks with VEGFR1_MOe13 or standard morpholino control. These constructs are prepared as detailed above. Tumor growth is assessed using digital calipers with biweekly measurements correlating with injection period. [Volume $[mm^3]=[width]^2 \times length/2$]. These animal studies are performed under IACUC protocol approval number 09-03005 approved by the Committee on the Ethics of Animal Experiments at the University of Utah. All interventions are performed either under sodium pentobarbital anesthesia or after animals are humanely euthanized.

Immunohistochemical Analysis:

Tumors are fixed in 4% paraformaldehyde for 2 h at 4 C, cryoprotected in 15% sucrose and 30% sucrose, and then embedded in OCT (Tissue-Tek, USA). Sections (12 um) are cut and were incubated with isolectin (Griffonia simplicifolia, Alexa Fluo568 conjugate 1:1000, Invitrogen Corporation, Carlsbad, Calif.) overnight. Immunohistochemistry results are examined using scanning laser confocal microscopy (Olympus, FLUOVIEW, FV1000, 20×).

These imagines are scored by Image-J morphometry system using biometry scoring (Wayne Rasband). After electroporation of F-MO (10 ul of 1 mM) or STD MO into HUVECs, the cells are plated to 8 well glass slide (nunc, Rochester, N.Y.) coated with collagen. 24 hours later, the cells are fixed with 4% paraformaldehyde/PBS, stained with DAPI, and observed with Carl Zeiss's inverted fluorescence microscope.

Statistical Analysis:

Data are presented as mean+/−SEM. Statistical analysis is performed using student T test. A p-value 0.05 is considered significant.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of inhibiting angiogenesis in a subject wherein the method comprises binding an antisense morpholino to a splicing site of VEGR1 mRNA in the subject wherein the splicing site is selected from the group consisting of exon13_intron13 junction, intron 13_exon14 junction, or a combination thereof such that the VEGFR1 mRNA is spliced into an sFlt-1 isoform, wherein the antisense morpholino is at least 75% identical to SEQ ID NO: 1 or is at least 75% identical to SEQ ID NO: 2.

2. The method of claim 1, wherein the antisense morpholino is selected from the group consisting of SEQ ID NO: 1, SEQ ID NO: 2, or a combination thereof.

3. The method of claim 1 wherein the antisense morpholino has a sequence that is at least 75% identical to SEQ ID NO: 1.

4. The method of claim 1 wherein the antisense morpholino has a sequence that is at least 95% identical to SEQ ID NO: 1.

5. The method of claim 1 wherein the antisense morpholino has the sequence of SEQ ID NO: 1.

6. The method of claim 1 wherein the antisense morpholino has a sequence that is at least 75% identical to SEQ ID NO: 2.

7. The method of claim 1 wherein the antisense morpholino has a sequence that is at least 95% identical to SEQ ID NO: 2.

8. The method of claim 1 wherein the antisense morpholino has the sequence of SEQ ID NO: 2.

9. A pharmaceutical composition for inhibiting angiogenesis in a subject, wherein the pharmaceutical composition comprises a pharmaceutically acceptable carrier and an antisense morpholino capable of binding to a splicing site of VEGR1 mRNA selected from the group consisting of exon13_intron13 junction, intron 13_exon14 junction, or a combination thereof, wherein the antisense morpholino is at least 75% identical to SEQ ID NO: 1 or is at least 75% identical to SEQ ID NO: 2.

10. The composition of claim 9, wherein the morpholino includes a member selected from the group consisting of VEGFR1$_{Moe}$13 (SEQ ID NO: 1), VEGFR1$_{MOi}$13 (SEQ ID NO: 2), or a combination thereof.

11. The composition of claim 9 wherein the antisense morpholino is at least 75% identical to SEQ ID NO: 1.

12. The composition of claim 9 wherein the antisense morpholino is at least 95% identical to SEQ ID NO: 1.

13. The composition of claim 9 wherein the antisense morpholino has the sequence of SEQ ID NO: 1.

14. The composition of claim 9 wherein the antisense morpholino is at least 75% identical to SEQ ID NO: 2.

15. The composition of claim 9 wherein the antisense morpholino is at least 95% identical to SEQ ID NO: 2.

16. The composition of claim 9 wherein the antisense morpholino has the sequence of SEQ ID NO: 2.

* * * * *

UNITED STATES PATENT AND TRADEMARK OFFICE
CERTIFICATE OF CORRECTION

PATENT NO. : 9,506,069 B2  
APPLICATION NO. : 14/394726  
DATED : November 29, 2016  
INVENTOR(S) : Balamurali K. Ambati and Hironori Uehara Page 1 of 1

It is certified that error appears in the above-identified patent and that said Letters Patent is hereby corrected as shown below:

In the Specification

Column 1; Line 13, should be corrected to read:

--GOVERNMENT INTEREST

This invention was made with government support under Grant Number GM021328 awarded by National Institutes of Health. The government has certain rights to this invention.--

Signed and Sealed this  
Seventh Day of March, 2017

Michelle K. Lee  
*Director of the United States Patent and Trademark Office*